United States Patent [19]

Altendorf

[11] Patent Number: 4,840,563

[45] Date of Patent: Jun. 20, 1989

[54] DENTAL EQUIPMENT HAVING MEANS FOR DELIVERING RF AND LF ENERGY TO A DENTAL HANDPIECE

[75] Inventor: Hans-Walter Altendorf, Worms, Fed. Rep. of Germany

[73] Assignee: Siemens Aktiengesellschaft, Berlin and Munich, Fed. Rep. of Germany

[21] Appl. No.: 155,115

[22] Filed: Feb. 11, 1988

[30] Foreign Application Priority Data

Feb. 26, 1987 [DE] Fed. Rep. of Germany ....... 3706265
Nov. 17, 1987 [DE] Fed. Rep. of Germany ....... 3739009

[51] Int. Cl.⁴ .............................................. A61C 3/00
[52] U.S. Cl. ..................................... 433/29; 433/119; 433/98; 174/36
[58] Field of Search ..................... 433/29, 27, 98, 119; 174/36

[56] References Cited

U.S. PATENT DOCUMENTS

| 3,076,904 | 2/1963 | Kleesattel et al. | 433/118 |
| 3,594,491 | 7/1971 | Zeidlhack | 174/36 |
| 3,809,977 | 5/1974 | Balamuth et al. | 433/119 |
| 3,930,173 | 12/1975 | Banko | 433/119 |
| 4,156,869 | 5/1979 | Schukantz | 174/115 |
| 4,578,033 | 3/1986 | Mossle et al. | 433/29 |
| 4,641,110 | 2/1987 | Smith | 174/36 |

OTHER PUBLICATIONS

Brochure labeled "Sirotom".

Primary Examiner—John J. Wilson

[57] ABSTRACT

Dental equipment having means for delivering RF and LF energy to a dental handpiece. Given a supply of RF energy, the dental equipment transmits a further energy that is significantly lower-frequency in comparison to the RF energy or a DC voltage for supplying a lamp located in the handpiece without disturbing influences. A common transmission cable is provided for the transmission of the RF energy and of the energy for the lamp, this common transmission cable contains an inner conductor and a shielded line arranged coaxially relative thereto and has a third conductor for transmission of the energy for the lamp. This third conductor is arranged relative to the shielded line such that a high capacitive coupling exists between shielded line and third conductor.

26 Claims, 1 Drawing Sheet

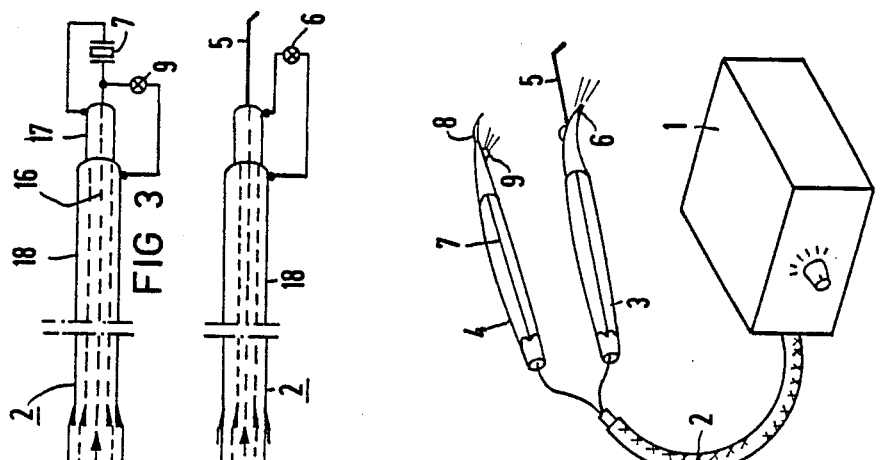
FIG 1
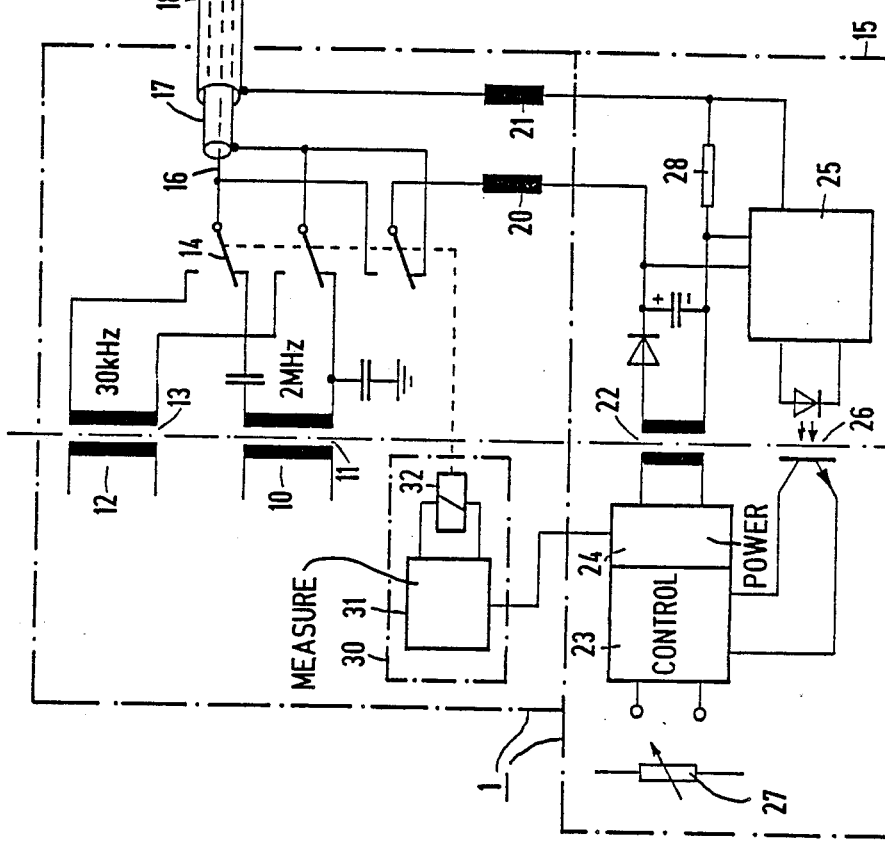
FIG 2
FIG 3

DENTAL EQUIPMENT HAVING MEANS FOR DELIVERING RF AND LF ENERGY TO A DENTAL HANDPIECE

BACKGROUND OF THE INVENTION

The present invention is directed to dental equipment having means for delivering energy to a dental handpiece that contains a tool. The tool can be subjected to ultrasound oscillations by a resonator arranged in the handpiece. Also, energy can be delivered to a dental handpiece that contains a surgical tool using radio-frequency current. A transmission cable is connected, first, to a supply part and, second to the handpiece. The transmission cable contains an inner conductor and a shielded line arranged coaxially thereto.

Radio frequency (RF) surgery handpieces as well as ultrasound handpieces are both known in dental medicine. Whereas ultrasound handpieces are usually used for removing deposits at the teeth, particularly for removing dental tartar, RF surgery handpieces are utilized for cutting and coagulating gingiva. Both piezoceramic transducers (as disclosed in U.S. Pat. No. 3,809,977) as well as magnetostrictive transducers (as disclosed in U.S. Pat. Nos. 3,076,904, and 3,930,173) are used for the excitation of the tool tip in ultrasound handpieces. The supply is located externally of the handpiece in both applications. The same is also true of RF surgery handpieces (apparatus bearing the designation "SIROTOM" of Siemens AG). Whereas the transducer for an ultrasound handpiece for removing dental tartar is operated with a frequency of about 30 kHz, i.e., in the lower RF region, surgical handpieces are operated with a frequency of about 2 MHz.

An object of the present invention in both types of handpiece is to be able to provide an illumination and/or display lamp that is usually operated with DC voltage or with a low frequency alternating voltage of about 50 through 100 Hz in a simple way without having disturbances arise in the transmission of the RF energy.

If the energy transmission for both energy forms were provided in the traditional way, i.e., with the assistance of a cable having immediately neighboring, parallel lines, then considerable disturbances or, respectively, mutual influencings would occur. Thus, sufficient RF power would flow to the lamp and would effect the lamps brightness dependent on the RF power set by the user. A destruction of the lamp could even be produced in the extreme case. A further disadvantage would result in that a part of the RF power would be used by the lamp, whereby a poorer efficiency would be established overall for the equipment. It is also a disadvantage that the lamp cannot be operated with a controlled voltage.

SUMMARY OF THE INVENTION

The equipment of the present invention provides a lamp that is supplied with a DC voltage or with a low frequency alternating voltage in addition to a handpiece which emits or, respectively, requires RF power, whereby both devices can be operated and may also be potentially controlled independently of one another without mutual, disturbing influencing.

The invention is especially advantageous when the equipment contains separate supply sources for, first a RF surgical handpiece and, second, an ultrasound handpiece for removing dental tartar and when switch-over means are used for connecting one or the other supply source to energy delivery lines of a transmission channel for a selected handpiece. Identification of the transmission energy required advantageously results from the lamp in both handpiece alternatives being connected to different conductors of a three-core cable. The circuit of the lamp is analyzed with a current or, respectively, a resistance measurement to see whether a lamp is present or not in this circuit. When a lamp is present in the circuit, then the applicable supply source is automatically switched to the handpiece provided with the lamp.

The three-core cable provided for transmission in the present invention assures that no RF power can flow into the lamp. It is advantageously formed as a triaxial cable whose first shielded conductor forms the RF energy carrier together with the inner conductor and whose second shielded conductor forms the energy carrier for the lamp together with the first shielded conductor. A conductor that is wound around the first shielded line can also be advantageously used instead of the triaxial cable.

For blocking the RF voltage relative to the voltage source for the lamp, the two shielded conductors are connected to the output of a clocked voltage source via inductances. For safety reasons, transformers having galvanic separation are provided both for the RF part as well as for the clocked voltage source.

In order to achieve a well-regulated voltage for the lamp despite separate windings and a poor coupling, a reference element having a measuring amplifier is provided at the secondary side of the clocked voltage source, this measuring amplifier containing a voltage reference and being supplied with the same voltage as the lamp. A preferably opto-electronic feedback element is provided between a control part and the reference element. Since the reference is situated at the secondary side, tolerances of the opto-coupler have no influence; they are largely compensated by the reference element that has a measuring amplifier. At the primary side of the clocked voltage source, the control part is provided with a control input for controlling the output voltage of the lamp. The supplied current can be advantageously measured via a fixed resistor that is arranged in the secondary circuit.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures in which like reference numerals identify like elements, and in which:

FIG. 1 is a perspective schematic drawing of dental equipment having a RF surgical handpiece and an ultrasound handpiece for removing dental tartar;

FIG. 2 is a circuit schematic in partial block diagram form showing details for the operation of the equipment according to FIG. 1 and having a simplified illustration of the connection of a RF surgical handpiece; and FIG. 3 is a simplified illustration of the connection of an ultrasound handpiece.

DESCRIPTION OF THE PREFERRED EMBODIMENT

FIG. 1 shows a simplified illustration of dental equipment having a supply part 1 to which either a RF surgical handpiece 3 or an ultrasound handpiece 4 for removing dental tartar can be alternatively connected with a transmission cable 2. As is known, the RF surgical handpiece 3 is equipped with a cutter or similar tool 5 to which RF power is output. A lamp 6 serving the purpose of illuminating the preparation location is provided immediately adjacent to the tool 5, the light exit location of this lamp 6 being directed approximately onto the tool tip.

The handpiece 4 for removing dental tartar contains an internal resonator 7 (piezo-electric or magnetostrictive) that is mechanically coupled to a tool 8 in a known way. The resonator is operated with a frequency of about 30 kHz, i.e. in the lower RF region. Just as in the case of the handpiece 3, a lamp 9 serving the purpose of illuminating the preparation location is also provided in the region of the tool 8 in the handpiece 4. The two lamps 6 and 9 are operated either with DC voltage or with low-frequency (LF) alternating voltage of 50-100 Hz.

The two handpieces are supplied, with, first, RF energy and, second, LF energy from the supply part 1 via the common transmission channel 2 which shall be set forth in yet greater detail below.

The structure of the supply part 1 is shown in FIG. 2. A RF part 10 that is constructed in a known way and that is provided with a transformer 11 has galvanic separation of primary and secondary circuits for safety reasons. Similarly, the RF part 12 in the handpiece for removing dental tartar has a transformer 13 which likewise has a galvanic separation of primary and secondary circuits.

Switch-over means 14 with which, first, the output of the RF part 10 or the output of the RF part 12 and, second, the output of a further supply source 15 can be alternatively connected to the lines of the transmission cable 2 will be explained in greater detail below.

The transmission cable 2 is a three-core cable that is fashioned as a triaxial cable in the present exemplary embodiment. The RF energy is transmitted from the RF generator 10 or, respectively, 12 onto the tool 5 or, respectively to the transducer 7 via the inner conductor 16. Together with a second, outer shielded conductor 18, the shielded conductor 17 arranged coaxially to the inner conductor 16 forms the input and output leads of the low-frequency energy for the lamps 6 or 9. When a RF surgical handpiece is employed, the lamp is connected between the shielded conductors 17,18 (FIG. 2); when the ultrasound handpiece for removing dental tartar is used, the lamp 9 is connected between inner conductor 16 and outer shielded line 18 (FIG. 3). The dimensioning of the coaxially arranged conductors 16,17,18 is based on the power to be transmitted and on the requirements of the RF energy generator. Since no great voltage insulations are required, the outer shielded conductor 18 lies over the shielded conductor 17 at only a slight distance. For example, a thin foil can serve as insulation. In the application, the operating voltage for the lamp is about 3.5 volts and draws a lamp current of 700 through 1200 mA. The output power thus is between 2 and 5 watts.

As a result of the coaxial arrangement of the two shielded conductors 17 and 18, there is a very strong capacitive coupling that prevents a RF voltage from shield to shield.

Instead of the triaxially arranged shielded conductors, it is also conceivable to wind the outer conductor around the shielded conductor 17, whereby an extremely strong capacitive coupling and, thus, a blocking of the RF energy carrier relative to the low-frequency energy carrier for feeding the lamps is provided.

The lamps 6 and 9 are supplied by a clocked voltage source 15 that is part of the supply part 1. In order to also prevent a blocking of the RF voltage relative to this voltage source 15, two inductances 20,21 are provided at the output of the voltage source 15. The clocked voltage source 15 contains a transformer 22 likewise having galvanic separation. The transformer 22 is operated by a control voltage source $U_{st}$. A control part 23 having a power part 24 is provided in the primary circuit of the voltage source 15 to form the control voltage source $U_{st}$.

In order to achieve a well-regulated voltage for the lamps 6 and 9 given the separate windings and the inherently poor coupling, a reference element 25 having a measured value amplifier is provided in the secondary circuit of the voltage source 15, this reference element 25 containing a voltage reference and being operated with the same voltage as the lamps 6 and 9. A feedback occurs via an opto-coupler 26. Since the reference is situated on the secondary side, tolerances of the opto-coupler have no influence; they are compensated by the measuring amplifier in the reference element 25.

The voltage drop appearing due to the two inductances 20 and 21, 0.5 volts each in the example, are compensated in the control part 23 at the primary side. The average operating current of the lamp is used as the controlling variable for the compensation.

The brightness of the lamps 6 and 9 can be influenced via an additional control input in the form, for example, of a voltage divider 27 with which the output voltage $U_{st}$ can be varied. In order to achieve a precise compensation of the voltage drop via the inductances 20 and 21, the compensation can also be performed by the reference element 25. To this end, a test resistor 28 can be provided at the secondary side of the transformer 22, the lamp current being measured with the use of this test resistor 28. This test resistor 28 will be expediently provided when the lamp resistance or, respectively, the lamp current are unknown. The voltage drop is measured via the resistor 28 and the voltage is then regulated such that the desired lamp voltage is present at the output following the two inductances, i.e. between the two shielded lines 17 and 18.

The switch-over means 14 is controlled dependent on the respective handpiece 3 or 4 that is connected. A control block 30 is provided for this purpose, containing a current-dependent or, respectively, voltage-dependent measuring element 31 with which the presence of the lamp 6 or, respectively, 9 for a connected handpiece 3 or 4 is identified by current measurement or resistance measurement. Given identification of the handpiece 4, for example, the control block 30 via a relay 32, causes the required switch-over from the one supply source 10 onto the other supply source 12.

A significant advantage of the equipment set forth above is that an ultrasound handpiece and a RF surgical handpiece can be provided with lamps whose energy supply is carried via the same connecting cable via which the RF energy is also transmitted. As a result of the automatic switch-over as a consequence of the handpiece identification, a very simple and reliable manipulation is achieved. The lamps can serve both for illuminating the preparation location as well as for displaying specific functions.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. Dental equipment having means for providing energy from a supply part to a first dental handpiece containing a tool that can be placed into ultrasound oscillations by a resonator located in said first handpiece and to a second dental handpiece containing a surgical tool operable with radio-frequency current (RF energy), by use of a transmission cable connectable, first, to said supply part and, second, to said first and second handpieces, said transmission cable containing at least an inner conductor and a shielded line arranged coaxially thereabout comprising:

said equipment containing an additional supply source for generating a lamp voltage having a frequency in the range of zero (DC voltage) to a significantly lower-frequency in comparison to the frequency of the RF energy for the operation of first and second lamps located in said first and second handpieces respectively; and said transmission cable provided for the transmission of, first, the RF energy and, second, the energy for the lamp, having a third conductor for the transmission of the lamp voltage for feeding the lamp, said third conductor being arranged relative to said shielded line such that a highly capacitive coupling exists between said shielded line and said third conductor.

2. The equipment according to claim 1, wherein a clock voltage source is provided as said additional supply source, said clock voltage source containing a transformer in whose primary circuit a control part is located for compensation of a voltage drop across inductances, said inductances being connected between an output of said additional supply source and said transmission cable; a reference element connected in the secondary circuit of said transformer, said reference element being supplied with the same voltage as the lamp; and an opto-electronic feedback element connected between said control part and said reference element.

3. The equipment according to claim 2, wherein said control part is provided with a control input for controlling the output voltage to said lamp.

4. The equipment according to claim 3, wherein a test resistor via which current flowing to said lamp is measured is connected to the secondary side of said transformer.

5. The equipment according to claim 1, wherein a first supply source is provided for generating RF energy for said electro-surgical handpiece and a second supply source is provided for transmitting RF energy to said transducer for the operation of said ultrasound handpiece for removing dental tartar; switch-over means connecting the one or the other supply source to the inner conductor and to the shielded line of the transmission cable of the appertaining handpiece dependent on the handpiece that is selected.

6. The equipment according to claim 5, wherein the lamp voltage for the lamp of a selected RF surgical handpiece is provided via the shielded line and via the third conductor and, the lamp voltage for the lamp of a selected ultrasound handpiece for removing dental tartar is provided via the inner conductor and the third conductor.

7. The equipment according to claim 5, wherein said switch-over means is switched by a control block that contains a current/voltage measuring element connected into the circuit of said lamp said voltage/current measuring element, given the presence of a lamp in the handpiece, connecting the transmission cable to that supply source of the first and second supply sources that is allocated to the handpiece provided with the lamp.

8. The equipment according to claim 1, wherein the third conductor is wound around the shielded line.

9. The equipment according to claim 1, wherein the third conductor is likewise fashioned as a shielded line and is arranged coaxially relative to the first shielded line.

10. Dental equipment having means for providing energy from a supply part to a first dental handpiece containing a tool that can be placed into ultrasound oscillations by a resonator located in said first handpiece and to a second dental handpiece containing a surgical tool operable with radio-frequency current (RF energy), a transmission cable connected between said supply part and said first and second handpieces, said transmission cable having at least an inner conductor and a shielded line arranged coaxially thereabout, comprising:

first and second lamps located in said first and second handpieces, respectively;

additional supply source for providing lamp voltage and connected to said first and second lamps via said transmission cable;

said transmission cable provided for transmitting said RF energy and said lamp voltage, said transmission cable having a third conductor for the transmission of the lamp voltage, said third conductor being arranged relative to said shielded line such that a highly capacitive coupling exists between said shielded line and said third conductor.

11. The equipment according to claim 10, wherein said lamp voltage is a DC voltage.

12. The equipment according to claim 10, wherein said lamp voltage has low-frequency energy in comparison to said RF energy.

13. The equipment according to claim 10, wherein a clock voltage source is provided as said additional supply source, said clock voltage source containing a transformer in whose primary circuit a control part is located for compensation of a voltage drop across inductances, said inductances being connected between an output of said additional supply source and said transmission cable; a reference element connected in the secondary circuit of said transformer, said reference element being supplied with the same voltage as the lamp; and an opto-electronic feedback element connected between said control part and said reference element.

14. The equipment according to claim 13, wherein said control part is provided with a control input for controlling the output voltage to said lamp.

15. The equipment according to claim 14, wherein a test resistor via which current flowing to said lamp is measured is connected to the secondary side of said transformer.

16. The equipment according to claim 10, wherein a first supply source is provided for generating RF energy for said electro-surgical handpiece and a second supply source is provided for transmitting RF energy to said transducer for the operation of said ultrasound handpiece for removing dental tartar; switch-over means connecting the one or the other supply source to the inner conductor and to the shielded line of the transmission cable of the appertaining handpiece dependent on the handpiece that is selected.

17. The equipment according to claim 16, wherein the lamp voltage for the lamp of a selected RF surgical handpiece is provided via the shielded line and via the third conductor and, the lamp voltage for the lamp of a selected ultrasound handpiece for removing dental tartar, is provided via the inner conductor and the third conductor.

18. The equipment according to claim 16, wherein said switch-over means is switched by a control block that contains a current/voltage measuring element connected into the circuit of said lamp, said voltage/current measuring element, given the presence of a lamp in the handpiece, connecting the transmission cable to that supply source of the first and second supply sources that is allocated to the handpiece provided with the lamp.

19. The equipment according to claim 10, wherein third conductor is would around the shielded line.

20. The equipment according to claim 10, wherein the third conductor is likewise fashioned as a shielded line and is arranged coaxially relative to the first shielded line.

21. Dental equipment having means for providing energy from a supply part to a dental handpiece containing a surgical tool operable with radio-frequency current (RF energy), by use of a transmission cable connectable, first, to said supply part and, second, to said handpiece, said transmission cable containing at least an inner conductor and a shielded line arranged coaxially thereabout comprising:

said equipment containing an additional supply source for generating a lamp voltage having a frequency in the range of zero (DC voltage) to a significantly lower-frequency in comparison to the frequency of the RF energy for the operation of the lamp located in said handpiece and said transmission cable provided for the transmission of, first, the RF energy and, second, the energy for the lamp, having a third conductor for the transmission of the lamp voltage for feeding the lamp, said third conductor being arranged relative to said shielded line such that a highly capacitive coupling exists between said shielded line and said third conductor.

22. The equipment according to claim 21, wherein a clock voltage source is provided as said additional supply source, said clock voltage source containing a transformer in whose primary circuit a control part is located for compensation of a voltage drop across inductances, said inductances being connected between an output of said additional supply source and said transmission cable; a reference element connected in the secondary circuit of said transformer, said reference element being supplied with the same voltage as the lamp; and an opto-electronic feedback element connected between said control part and said reference element.

23. The equipment according to claim 22, wherein said control part is provided with a control input for controlling the output voltage to said lamp.

24. The equipment according to claim 23, wherein a test resistor via which current flowing to said lamp is measured is connected to the secondary side of said transformer.

25. The equipment according to claim 21, wherein the third conductor is wound around the shielded line.

26. The equipment according to claim 21, wherein the third conductor is likewise fashioned as a shielded line and is arranged coaxially relative to the first shielded line.

* * * * *